(12) United States Patent
Zacher et al.

(10) Patent No.: US 11,382,736 B2
(45) Date of Patent: Jul. 12, 2022

(54) INJECTOR, INTRAOCULAR LENS SYSTEM, AND RELATED METHODS

(71) Applicant: ClarVista Medical, Inc., Aliso Viejo, CA (US)

(72) Inventors: Rudolph F. Zacher, Trabuco Canyon, CA (US); Glenn Sussman, Laguna Niguel, CA (US); Jason H. Safabash, Mission Viejo, CA (US)

(73) Assignee: Alcon Inc., Fribourg (CH)

( * ) Notice: Subject to any disclaimer, the term of this patent is extended or adjusted under 35 U.S.C. 154(b) by 56 days.

(21) Appl. No.: 16/017,369

(22) Filed: Jun. 25, 2018

(65) Prior Publication Data
US 2018/0368971 A1    Dec. 27, 2018

Related U.S. Application Data

(60) Provisional application No. 62/534,988, filed on Jul. 20, 2017, provisional application No. 62/525,317, filed on Jun. 27, 2017.

(51) Int. Cl.
*A61F 2/16* (2006.01)
*A61F 2/14* (2006.01)

(52) U.S. Cl.
CPC .............. *A61F 2/167* (2013.01); *A61F 2/16* (2013.01); *A61F 2/15* (2015.04);
(Continued)

(58) Field of Classification Search
CPC ............ A61F 2/1691; A61F 2002/1681; A61F 2002/16902
See application file for complete search history.

(56) References Cited

U.S. PATENT DOCUMENTS

| 3,937,222 A | | 2/1976 | Banko | |
|---|---|---|---|---|
| 4,092,743 A | * | 6/1978 | Kelman | ................... A61F 2/16 623/6.43 |

(Continued)

FOREIGN PATENT DOCUMENTS

| CA | 3 002 085 A1 | 5/2017 |
|---|---|---|
| CN | 101039635 A | 9/2007 |

(Continued)

OTHER PUBLICATIONS

PCT International Search Report and Written Opinion for International Application No. PCT/US2013/022752, dated Apr. 19, 2013 (12 pages).

(Continued)

*Primary Examiner* — Alexander J Orkin
(74) *Attorney, Agent, or Firm* — Bookoff McAndrews, PLLC

(57) ABSTRACT

An intraocular lens system may include a base that may include an annular body, an opening extending through the annular body in an axial direction of the annular body, and a recess extending circumferentially about the opening. The system also may include a lens that may be insertable into and removable from the recess. The lens may include a central optic, a first tab protruding radially away from the central optic, and a second tab protruding radially away from the central optic. The second tab may be more resistant to compression in a radial direction than the first tab. The first tab may include a first arm protruding radially away from the central optic, a second arm protruding radially away from the central optic and extending away from the first arm, and a third arm extending from the first arm to the second arm. Movement of one or more of the first, second, and third arms may result in deformation of the first tab.

18 Claims, 11 Drawing Sheets

(52) U.S. Cl.
CPC ............... *A61F 2002/1681* (2013.01); *A61F 2002/1686* (2013.01); *A61F 2002/16902* (2015.04); *A61F 2220/0033* (2013.01); *A61F 2240/001* (2013.01); *A61F 2250/0014* (2013.01)

(56) References Cited

U.S. PATENT DOCUMENTS

| | | | |
|---|---|---|---|
| 4,168,547 A | 9/1979 | Konstantinov et al. | |
| 4,409,691 A | 10/1983 | Levy | |
| 4,435,856 A | 3/1984 | L'Esperance | |
| 4,681,102 A | 7/1987 | Bartell | |
| 4,693,245 A | 9/1987 | Pao | |
| 4,741,330 A | 5/1988 | Hayhurst | |
| 4,769,035 A | 11/1988 | Kelman | |
| 4,816,031 A | 3/1989 | Pfoff | |
| 4,828,558 A | 5/1989 | Kelman | |
| 4,842,601 A | 6/1989 | Smith | |
| 4,878,910 A | 11/1989 | Koziol et al. | |
| 4,911,715 A | 3/1990 | Kelman | |
| 4,932,971 A | 6/1990 | Kelman | |
| 4,950,272 A | 8/1990 | Smirmaul | |
| 4,960,418 A | 10/1990 | Tennant | |
| 5,026,396 A | 6/1991 | Darin | |
| 5,030,230 A | 7/1991 | White | |
| 5,098,444 A | 3/1992 | Feaster | |
| 5,123,905 A | 6/1992 | Kelman | |
| 5,133,747 A | 7/1992 | Feaster | |
| 5,147,369 A | 9/1992 | Wagner | |
| 5,152,788 A | 10/1992 | Isaacson et al. | |
| 5,201,762 A | 4/1993 | Hauber | |
| 5,222,981 A | 6/1993 | Werblin | |
| 5,304,182 A | 4/1994 | Rheinsish et al. | |
| 5,354,335 A | 10/1994 | Lipshitz et al. | |
| 5,358,520 A | 10/1994 | Patel | |
| 5,366,502 A | 11/1994 | Patel | |
| 5,378,475 A | 1/1995 | Smith et al. | |
| 5,391,202 A | 2/1995 | Lipshitz et al. | |
| 5,395,378 A | 3/1995 | McDonald | |
| 5,410,375 A | 4/1995 | Fiala | |
| 5,417,369 A | 5/1995 | Lipson | |
| 5,507,805 A | 4/1996 | Koeniger | |
| 5,578,081 A | 11/1996 | McDonald | |
| 5,616,120 A | 4/1997 | Andrew et al. | |
| 5,628,795 A | 5/1997 | Langerman | |
| 5,628,798 A | 5/1997 | Eggleston et al. | |
| 5,728,155 A | 3/1998 | Anello et al. | |
| 5,769,890 A | 6/1998 | McDonald | |
| 5,814,103 A | 9/1998 | Lipshitz et al. | |
| 5,824,074 A | 10/1998 | Koch | |
| 5,860,985 A | 1/1999 | Anschutz | |
| 5,876,442 A | 3/1999 | Lipshitz et al. | |
| 5,895,422 A | 4/1999 | Hauber | |
| 5,902,598 A | 5/1999 | Chen et al. | |
| 5,928,283 A | 7/1999 | Gross et al. | |
| 5,944,725 A | 8/1999 | Cicenas et al. | |
| 5,964,802 A | 10/1999 | Anello et al. | |
| 5,968,094 A | 10/1999 | Werblin et al. | |
| 5,984,962 A | 11/1999 | Anello et al. | |
| 6,027,531 A | 2/2000 | Tassignon | |
| 6,066,171 A | 5/2000 | Lipshitz et al. | |
| 6,113,633 A | 9/2000 | Portney | |
| 6,136,026 A | 10/2000 | Israel | |
| 6,197,057 B1 | 3/2001 | Peyman et al. | |
| 6,197,058 B1 | 3/2001 | Portney | |
| 6,197,059 B1* | 3/2001 | Cumming | ............ B29D 11/026 623/6.39 |
| 6,228,113 B1 | 5/2001 | Kaufman | |
| 6,231,603 B1 | 5/2001 | Lang et al. | |
| 6,277,146 B1 | 8/2001 | Peyman et al. | |
| 6,280,471 B1 | 8/2001 | Peyman et al. | |
| 6,358,280 B1 | 3/2002 | Herrick | |
| 6,413,276 B1 | 7/2002 | Werblin | |
| 6,423,094 B1 | 7/2002 | Sarfarazi | |
| 6,454,801 B1 | 9/2002 | Portney | |
| 6,464,725 B2 | 10/2002 | Skotton | |
| 6,488,708 B2 | 12/2002 | Sarfarazi | |
| 6,537,281 B1 | 3/2003 | Portney | |
| 6,551,354 B1 | 4/2003 | Ghazizadeh et al. | |
| 6,554,859 B1 | 4/2003 | Lang et al. | |
| 6,558,420 B2 | 5/2003 | Green | |
| 6,596,026 B1 | 7/2003 | Gross et al. | |
| 6,599,317 B1 | 7/2003 | Weinschenk, III et al. | |
| 6,616,692 B1 | 9/2003 | Glick et al. | |
| 6,638,304 B2 | 10/2003 | Azar | |
| 6,685,741 B2 | 2/2004 | Landreville et al. | |
| 6,695,881 B2 | 2/2004 | Peng et al. | |
| 6,764,511 B2 | 7/2004 | Zadno-Azizi et al. | |
| 6,767,363 B1 | 7/2004 | Bandhauer et al. | |
| 6,786,934 B2 | 9/2004 | Zadno-Azizi et al. | |
| 6,797,004 B1 | 9/2004 | Brady et al. | |
| 6,818,017 B1 | 11/2004 | Shu | |
| 6,846,326 B2 | 1/2005 | Zadno-Azizi et al. | |
| 6,858,040 B2 | 2/2005 | Nguyen et al. | |
| 6,899,732 B2 | 5/2005 | Zadno-Azizi et al. | |
| 6,926,736 B2 | 8/2005 | Peng et al. | |
| 6,960,231 B2 | 11/2005 | Tran | |
| 6,969,403 B2 | 11/2005 | Peng et al. | |
| 6,972,032 B2 | 12/2005 | Aharoni et al. | |
| 6,972,034 B2 | 12/2005 | Tran et al. | |
| 6,991,651 B2 | 1/2006 | Portney | |
| 7,008,447 B2 | 3/2006 | Koziol | |
| 7,041,134 B2 | 5/2006 | Nguyen et al. | |
| 7,081,134 B2 | 7/2006 | Cukrowski | |
| 7,087,080 B2 | 8/2006 | Zadno-Azizi et al. | |
| 7,097,660 B2 | 8/2006 | Portney | |
| 7,101,397 B2 | 9/2006 | Aharoni | |
| 7,118,596 B2 | 10/2006 | Zadno-Azizi et al. | |
| 7,122,053 B2 | 10/2006 | Esch | |
| 7,125,422 B2 | 10/2006 | Woods et al. | |
| 7,186,266 B2 | 3/2007 | Peyman | |
| 7,198,640 B2 | 4/2007 | Nguyen | |
| 7,220,278 B2 | 5/2007 | Peyman | |
| 7,223,288 B2 | 5/2007 | Zhang et al. | |
| 7,226,478 B2 | 6/2007 | Ting et al. | |
| 7,238,201 B2 | 7/2007 | Portney et al. | |
| 7,300,464 B2 | 11/2007 | Tran | |
| 7,316,713 B2 | 1/2008 | Zhang | |
| 7,452,378 B2 | 11/2008 | Zadno-Azizi et al. | |
| 7,582,113 B2 | 9/2009 | Terwee | |
| 7,591,849 B2 | 9/2009 | Richardson | |
| 7,645,299 B2 | 1/2010 | Koziol | |
| 7,662,179 B2 | 2/2010 | Sarfarazi | |
| 7,727,277 B2 | 6/2010 | Aharoni et al. | |
| 7,736,390 B2 | 6/2010 | Aharoni et al. | |
| 7,780,729 B2 | 8/2010 | Nguyen et al. | |
| 7,811,320 B2 | 10/2010 | Werblin | |
| 7,857,850 B2 | 12/2010 | Mentak et al. | |
| 7,871,437 B2 | 1/2011 | Hermans et al. | |
| 7,918,886 B2 | 4/2011 | Aharoni et al. | |
| 7,985,253 B2 | 7/2011 | Cumming | |
| 7,993,399 B2 | 8/2011 | Peyman | |
| 7,998,198 B2 | 8/2011 | Angelopoulos et al. | |
| 8,012,204 B2 | 9/2011 | Weinschenk, III et al. | |
| 8,034,106 B2 | 10/2011 | Mentak et al. | |
| 8,034,107 B2 | 10/2011 | Stenger | |
| 8,034,108 B2 | 10/2011 | Bumbalough | |
| 8,062,361 B2 | 11/2011 | Nguyen et al. | |
| 8,066,768 B2 | 11/2011 | Werblin | |
| 8,066,769 B2 | 11/2011 | Werblin | |
| 8,128,693 B2 | 3/2012 | Tran et al. | |
| 8,137,399 B2 | 3/2012 | Glazier et al. | |
| 8,167,941 B2 | 5/2012 | Boyd et al. | |
| 8,182,531 B2 | 5/2012 | Hermans et al. | |
| 8,187,325 B2 | 5/2012 | Zadno-Azizi et al. | |
| 8,197,541 B2 | 6/2012 | Schedler | |
| 8,273,123 B2 | 9/2012 | Ben Nun | |
| 8,287,593 B2 | 10/2012 | Portney | |
| 8,377,124 B2 | 2/2013 | Hong et al. | |
| 8,425,597 B2 | 4/2013 | Glick et al. | |
| 8,486,142 B2 | 7/2013 | Bumbalough | |
| 8,579,972 B2* | 11/2013 | Rombach | ............ A61F 2/1613 623/6.34 |
| 8,663,235 B2 | 3/2014 | Tassignon | |

(56) References Cited

U.S. PATENT DOCUMENTS

| | | |
|---|---|---|
| 8,728,158 B2 | 5/2014 | Whitsett |
| 8,758,434 B2 | 6/2014 | Scott |
| 8,900,300 B1 | 12/2014 | Wortz |
| 9,011,532 B2 | 4/2015 | Bumbalough |
| 9,095,424 B2 | 8/2015 | Kahook et al. |
| 9,125,736 B2 | 9/2015 | Kahook |
| 9,198,752 B2 | 12/2015 | Woods |
| 9,204,961 B2 | 12/2015 | Cuevas |
| 9,220,590 B2 | 12/2015 | Beer |
| 9,289,287 B2 | 3/2016 | Kahook |
| 9,364,316 B1 | 6/2016 | Kahook |
| 9,387,069 B2 | 7/2016 | Kahook et al. |
| 9,414,907 B2 | 8/2016 | Wortz et al. |
| 9,421,088 B1 | 8/2016 | Kahook et al. |
| 9,504,558 B2 | 11/2016 | Wortz et al. |
| 9,517,127 B2 | 12/2016 | Wortz et al. |
| 9,522,059 B2 | 12/2016 | Wortz et al. |
| 9,522,060 B2 | 12/2016 | Wortz et al. |
| 9,681,946 B2 | 6/2017 | Kahook et al. |
| 9,877,825 B2 | 1/2018 | Kahook et al. |
| 9,925,040 B2 | 3/2018 | Kahook et al. |
| 10,028,824 B2 | 7/2018 | Kahook et al. |
| 10,080,648 B2 | 9/2018 | Kahook et al. |
| 2002/0138140 A1* | 9/2002 | Hanna .................. A61F 2/1613 623/6.37 |
| 2003/0088253 A1 | 5/2003 | Seil |
| 2003/0144733 A1 | 7/2003 | Brady et al. |
| 2003/0158560 A1 | 8/2003 | Portney |
| 2004/0010310 A1 | 1/2004 | Peyman |
| 2004/0106993 A1 | 6/2004 | Portney |
| 2004/0148022 A1 | 7/2004 | Eggleston |
| 2004/0236422 A1 | 11/2004 | Zhang et al. |
| 2004/0243142 A1 | 12/2004 | Siepser |
| 2005/0015144 A1 | 1/2005 | Tran |
| 2005/0021139 A1 | 1/2005 | Shadduck |
| 2005/0027354 A1 | 2/2005 | Brady et al. |
| 2005/0187621 A1 | 5/2005 | Brady |
| 2005/0125058 A1 | 6/2005 | Cumming et al. |
| 2005/0131535 A1 | 6/2005 | Woods |
| 2005/0273163 A1 | 12/2005 | Tran et al. |
| 2006/0111776 A1 | 5/2006 | Glick et al. |
| 2006/0253196 A1 | 11/2006 | Woods |
| 2006/0286147 A1 | 12/2006 | Salamone et al. |
| 2007/0052923 A1 | 3/2007 | Ayyagari et al. |
| 2007/0123981 A1 | 5/2007 | Tassignon |
| 2007/0156236 A1 | 7/2007 | Stenger |
| 2008/0046077 A1 | 2/2008 | Cumming |
| 2008/0103592 A1 | 5/2008 | Maloney |
| 2008/0215147 A1 | 9/2008 | Werblin |
| 2008/0281416 A1 | 11/2008 | Cumming |
| 2009/0005864 A1 | 1/2009 | Eggleston |
| 2010/0016964 A1 | 1/2010 | Werblin |
| 2010/0204787 A1 | 8/2010 | Noy |
| 2010/0204790 A1 | 8/2010 | Whitsett |
| 2010/0298933 A1 | 11/2010 | Knox et al. |
| 2011/0040378 A1 | 2/2011 | Werblin |
| 2011/0054600 A1 | 3/2011 | Bumbalough |
| 2011/0251686 A1 | 10/2011 | Masket |
| 2011/0257742 A1 | 10/2011 | Bumbalough |
| 2011/0307058 A1 | 12/2011 | Beer |
| 2011/0313521 A1 | 12/2011 | Angelopoulos |
| 2012/0078364 A1 | 3/2012 | Stenger |
| 2012/0179249 A1 | 7/2012 | Coleman |
| 2012/0209305 A1 | 8/2012 | Deodhar et al. |
| 2012/0323320 A1 | 12/2012 | Simonov et al. |
| 2013/0066422 A1* | 3/2013 | Dworschak ........... A61F 2/1613 623/6.51 |
| 2013/0184815 A1 | 7/2013 | Roholt |
| 2013/0190868 A1 | 7/2013 | Kahook et al. |
| 2013/0296694 A1 | 11/2013 | Ehlers et al. |
| 2013/0304204 A1 | 11/2013 | Bumbalough |
| 2013/0304206 A1 | 11/2013 | Pallikaris et al. |
| 2013/0310931 A1 | 11/2013 | Kahook et al. |
| 2014/0052246 A1 | 2/2014 | Kahook et al. |
| 2014/0081178 A1 | 3/2014 | Pletcher et al. |
| 2014/0084489 A1 | 3/2014 | Etzkorn |
| 2014/0085599 A1 | 3/2014 | Etzkorn |
| 2014/0085600 A1 | 3/2014 | Pletcher et al. |
| 2014/0085602 A1 | 3/2014 | Ho et al. |
| 2014/0087452 A1 | 3/2014 | Liu et al. |
| 2014/0088381 A1 | 3/2014 | Etzkorn et al. |
| 2014/0098226 A1 | 4/2014 | Pletcher et al. |
| 2014/0180411 A1 | 6/2014 | Tornambe et al. |
| 2014/0192311 A1 | 7/2014 | Pletcher et al. |
| 2014/0194710 A1 | 7/2014 | Ho et al. |
| 2014/0194713 A1 | 7/2014 | Liu |
| 2014/0194773 A1 | 7/2014 | Pletcher et al. |
| 2014/0371852 A1 | 12/2014 | Aharoni et al. |
| 2015/0157452 A1 | 6/2015 | Maliarov |
| 2015/0230981 A1 | 8/2015 | Kahook et al. |
| 2016/0074154 A1 | 3/2016 | Woods |
| 2016/0157995 A1 | 6/2016 | Beer |
| 2016/0184089 A1 | 6/2016 | Dudee et al. |
| 2016/0235524 A1 | 8/2016 | Wortz et al. |
| 2016/0235587 A1 | 8/2016 | Kahook et al. |
| 2016/0310264 A1 | 10/2016 | Akura |
| 2016/0338825 A1 | 11/2016 | Wortz et al. |
| 2017/0119521 A1 | 5/2017 | Kahook et al. |
| 2017/0319332 A1* | 11/2017 | Kahook ................ A61F 2/1648 |
| 2018/0271645 A1* | 9/2018 | Brady ..................... G02C 7/08 |

FOREIGN PATENT DOCUMENTS

| | | |
|---|---|---|
| CN | 101641060 A | 2/2010 |
| CN | 104936553 A | 9/2015 |
| DE | 10 2007 053 224 A1 | 5/2009 |
| EP | 0478929 A1 | 4/1992 |
| EP | 1 138 282 | 10/2001 |
| EP | 1 457 170 A1 | 9/2004 |
| EP | 1 743 601 A1 | 1/2007 |
| EP | 1 862 147 A1 | 12/2007 |
| EP | 2 042 124 A1 | 4/2009 |
| EP | 2332501 A1 | 6/2011 |
| EP | 1 296 616 B1 | 5/2012 |
| EP | 1 871 299 B1 | 8/2012 |
| EP | 2491902 B1 | 8/2012 |
| JP | 62-022641 | 1/1987 |
| JP | 01-097450 | 4/1989 |
| JP | 04-505715 | 10/1992 |
| JP | 06-165793 | 6/1994 |
| JP | 06-189985 | 7/1994 |
| JP | 63-089154 | 4/1998 |
| JP | 2003-505197 | 2/2003 |
| JP | 2003-524503 | 8/2003 |
| JP | 2007-512907 | 5/2007 |
| JP | 2008-532617 | 8/2008 |
| JP | 2010-516394 | 5/2010 |
| JP | 2012-040326 | 3/2012 |
| JP | 2013-512033 | 4/2013 |
| JP | 5705529 B2 | 4/2015 |
| RU | 2026652 C1 | 1/1995 |
| WO | WO 94/28825 A1 | 12/1994 |
| WO | WO 96/29956 A1 | 10/1996 |
| WO | WO 03/039335 A2 | 5/2003 |
| WO | WO 2006/023871 A2 | 3/2006 |
| WO | WO 2006/118452 A1 | 11/2006 |
| WO | WO 2008/094518 A1 | 8/2008 |
| WO | WO 2008/108524 A1 | 9/2008 |
| WO | WO 2010/002215 A2 | 1/2010 |
| WO | WO 2011/065833 A1 | 6/2011 |
| WO | WO 2012/023133 A1 | 2/2012 |
| WO | WO 2013/112589 A1 | 8/2013 |
| WO | WO 2013/158942 A1 | 10/2013 |
| WO | WO 2014/099604 A1 | 6/2014 |
| WO | WO 2014/197170 A1 | 12/2014 |
| WO | WO 2014/204575 A1 | 12/2014 |
| WO | WO 2016/022995 A2 | 2/2016 |
| WO | WO 2016/130209 A1 | 8/2016 |

OTHER PUBLICATIONS

PCT International Search Report and Written Opinion for Interna-

(56) References Cited

OTHER PUBLICATIONS tional Application No. PCT/US2014/037646, dated Aug. 18, 2014 (14 pages).
PCT International Search Report and Written Opinion for International Application No. PCT/US2015/014046, dated Apr. 9, 2015 (14 pages).
PCT International Search Report and Written Opinion for International Application No. PCT/US2015/067035, dated Apr. 12, 2016 (17 pages).
PCT International Search Report and Written Opinion for International Application No. PCT/US2016/060350, dated Jan. 27, 2017 (14 pages).

* cited by examiner

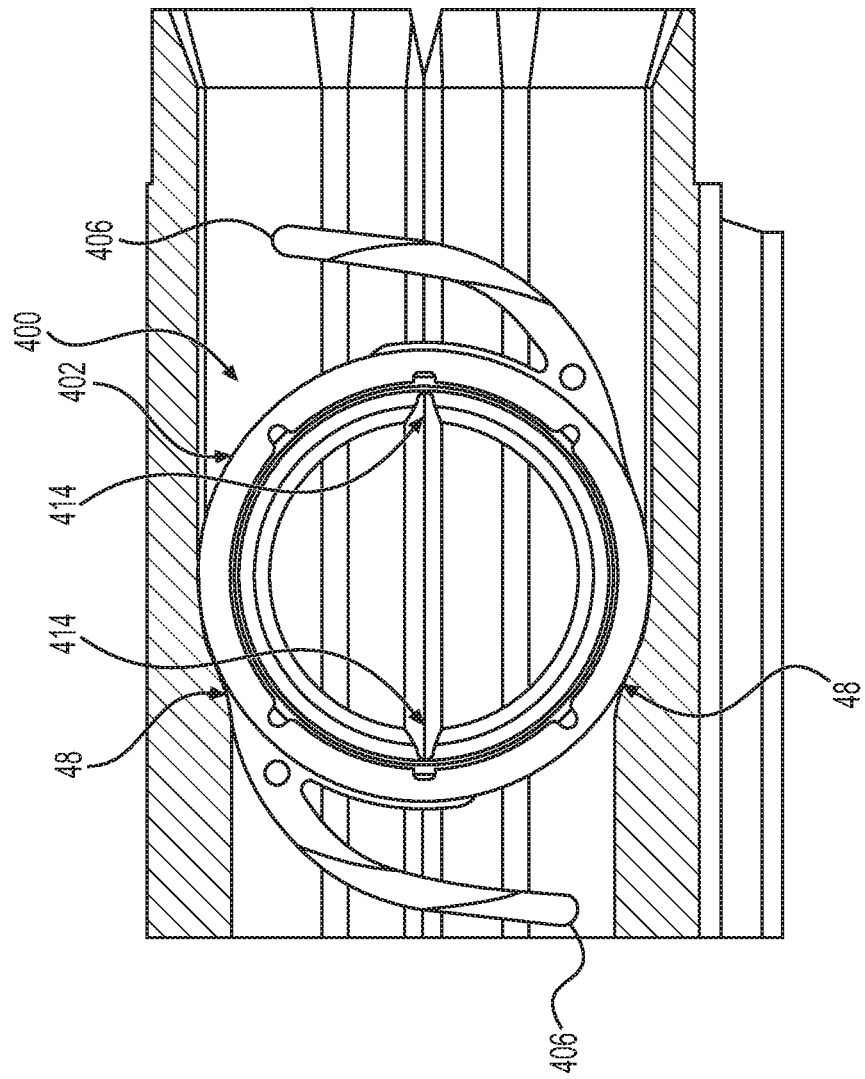

INJECTOR, INTRAOCULAR LENS SYSTEM, AND RELATED METHODS

CROSS-REFERENCE TO RELATED APPLICATIONS

This patent application claims the benefit under 35 U.S.C. § 119 to U.S. Provisional Patent Application No. 62/525,317, filed on Jun. 27, 2017; and to U.S. Provisional Patent Application No. 62/534,988, filed on Jul. 20, 2017, each of which is incorporated herein by reference in its entirety.

TECHNICAL FIELD

The present disclosure generally relates to intraocular lens (IOL) systems and related injectors. More specifically, the present disclosure relates to various embodiments of modular IOL systems and injector designs for improved injection of IOL components into an eye.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent (e.g., cloudy), vision deteriorates because of the diminished light, which can be transmitted to the retina. This deficiency in the lens of the eye is medically known as a cataract.

An accepted treatment for this condition is surgical removal of the lens from the capsular bag and placement of an artificial intraocular lens (IOL) in the capsular bag. Cataractous lenses are removed by a surgical technique called phacoemulsification. During this procedure, an opening (capsulorhexis) is made in the anterior side of the capsular bag and a thin phacoemulsification-cutting tip is inserted into the diseased lens and vibrated ultrasonically. The vibrating cutting tip emulsifies the lens so that the lens may be aspirated out of the capsular bag.

The diseased lens, once removed, is replaced by an IOL that is inserted into the eye using an injector, and maneuvered into the empty capsular bag. In some instances, the IOL may become stuck in the injector, or the IOL may become damaged as a result of poor technique or training, as in the case of a damaged trailing IOL haptic. Improvements in injector design are needed to address this problem.

SUMMARY

Embodiments of the present disclosure provide an injector for injecting one or more components of an IOL system into the eye, the injector having a housing, a cartridge for holding the IOL system component, a distal nozzle having a tapered lumen and a plunger having a tip disposed in a channel of the housing. The plunger tip may have two arms that change from an expanded configuration when disposed in the proximal end of the nozzle lumen and a contracted configuration when disposed in the distal end of the nozzle lumen.

The arms may have a gap between them that decreases as the arms pass through the nozzle. The arms may remain in contact with the inner wall of the nozzle lumen as the arms pass through the nozzle. The distal ends of the arms may be free or attached to a collapsible link, for example. The arms may include inwardly extending fingers that are offset relative to each other such that they bypass each other as the arms move toward each other. The fingers may be configured to prevent the IOL system component from passing through the gap between the arms.

The distal end of the arms or the distal end of the link may include a bevel with a distal-most edge and a distal-facing surface. The distal-facing surface may be configured to engage and push the IOL system component. The distal-most edge may be in contact with the inner wall of the nozzle lumen to prevent the IOL system component from passing between the arm and the inner wall as the IOL system component passes through the nozzle.

Embodiments of the present disclosure also provide a modular IOL system comprising a primary component, such as a base, and a secondary component, such as a lens.

According to one aspect of the present disclosure, an intraocular lens system may include a base that may include an annular body, an opening extending through the annular body in an axial direction of the annular body, and a recess extending circumferentially about the opening. The system also may include a lens that may be insertable into and removable from the recess. The lens may include a central optic, a first tab protruding radially away from the central optic, and a second tab protruding radially away from the central optic. The second tab may be more resistant to compression in a radial direction than the first tab. The first tab may include a first arm protruding radially away from the central optic, a second arm protruding radially away from the central optic and extending away from the first arm, and a third arm extending from the first arm to the second arm. Movement of one or more of the first, second, and third arms may result in deformation of the first tab.

According to another aspect of the present disclosure, an intraocular lens system may include a base including an annular body, an opening extending through the annular body in an axial direction of the annular body, and a recess extending circumferentially about the opening. The system also may include a lens configured for insertion into and removable from the recess. The lens may include a central optic, a first tab extending radially away from the central optic, and a second tab extending radially away from the central optic. The second tab may be more resistant to compression than the first tab. The first tab may include a first arm extending radially away from the central optic, a second arm extending radially away from the central optic, and a third arm extending between the first arm with the second arm. One or more of the first, second, and third arms is configured to deform to move the first tab between a compressed state and an extended state. In the extended state of the first tab, an obtuse angle may be formed between the first and second arms.

According to another aspect of the present disclosure, a method for assembling an intraocular lens system may include inserting one of: (a) a first tab and (b) a second tab, of a lens of the intraocular lens system, into a recess of a base of the intraocular lens system. The second tab may be more resistant to compression than the first tab. The lens may include a central optic, the first tab extending radially away from the central optic, and the second tab extending radially from the central optic. The first tab may include a first arm extending radially away from the central optic, a second arm extending radially away from the central optic and away from the first arm, and a third arm linking the first and second arms. The base may include an annular body and an opening extending through the annular body in an axial direction of the annular body. The recess may extend circumferentially about the opening. The method also may include inserting the other of the first and second tabs into the recess. The other of the first and second tabs may be inserted into the recess while the at least one of the first and second tabs is in the recess.

Various other aspects and advantages of embodiments of the present disclosure are described in the following detailed description and drawings. It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure. The drawings are not necessarily to scale, may include similar elements that are numbered the same, and may include dimensions (in millimeters) and angles (in degrees) by way of example, not necessarily limitation. In the drawings:

FIG. 7C is the same cross-sectional view shown in FIG. 7B with a base positioned therein;

DETAILED DESCRIPTION

Overview

The following detailed description describes various embodiments of IOL system injectors. Features described with reference to any one embodiment may be applied to and incorporated into other embodiments.

Exemplary Embodiments

Figure 1A:
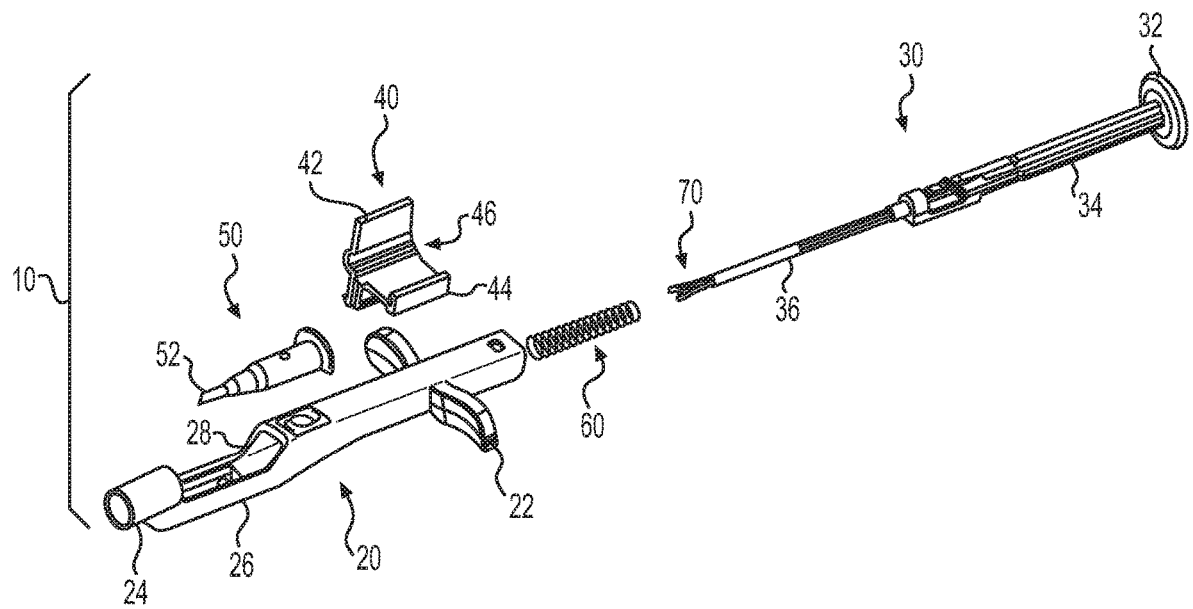
FIG. 1A is an exploded view of an IOL system injector according to an embodiment of the present disclosure.

With reference to FIG. 1A, IOL system injector 10 generally includes an injector housing 20, a plunger 30, a loading cartridge 40, a nozzle (a.k.a. cartridge tip) 50 and a spring 60. The housing 20 includes finger grips 22, a nozzle holder 24, a cartridge holder 26 and an internal channel 28 extending therethrough. The plunger 30 includes a thumb pad 32, a proximal shaft 34, a distal shaft 36 and a plunger tip 70. The IOL system loading cartridge 40 includes a first folding wing 42, a second folding wing 44 with a locking mechanism, and a chamber 46 configured to hold the IOL system when the wings 42, 44 are closed. The nozzle 50 includes an internal lumen (not visible) that has a decreasing cross-sectional area proximal to distal. The nozzle 50 also includes a beveled tip 52 for insertion into the incision in the eye.

Figure 1B:
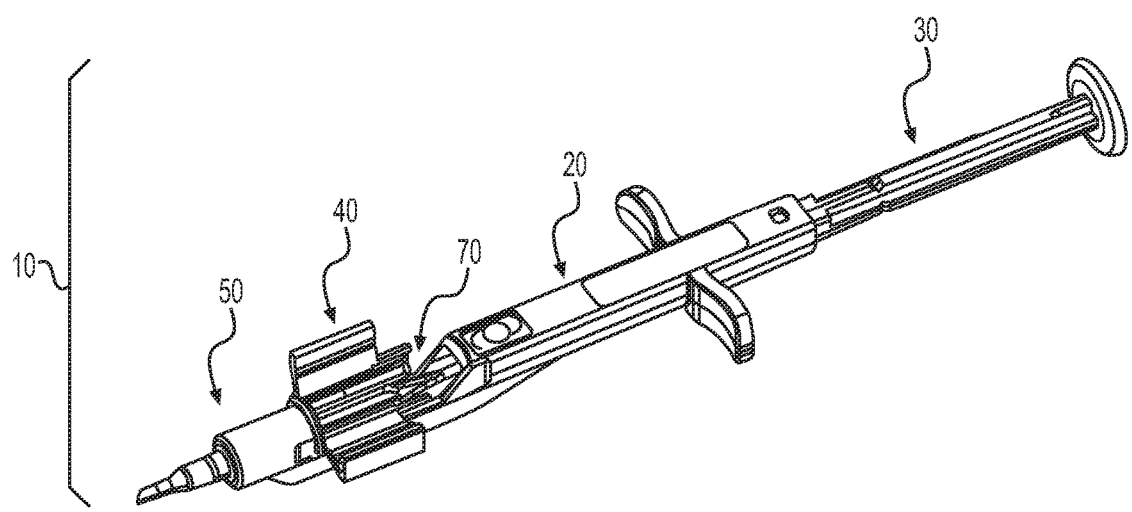
FIG. 1B is an assembly view of the IOL system injector shown in FIG. 1A.

The injector 10 is modular in nature such that the nozzle 50 may be inserted into the nozzle holder 24 of the housing 20, the cartridge may be inserted into the cartridge holder 26 of the housing 20, the spring 60 may be disposed on the distal shaft 36 of the plunger 30, and the plunger 30 together with spring 60 may be inserted into the channel 28 of the housing 20 to form an assembled IOL system injector 10 as shown in FIG. 1B.

With this arrangement, an IOL system component may be loaded or pre-loaded in the chamber 46 of the loading cartridge 40. The loading cartridge 40 is placed in the cartridge holder 26 in the housing 20. Then, the wings 42, 44 are folded or closed to essentially roll or fold the IOL system component such that it has a reduced profile suitable for injection. Using one hand with two fingers on the finger grips 22 of the housing 20 and a thumb on the thumb pad 32 of the plunger 30, the plunger 30 may be advanced distally through the channel 28 in the housing 20 until the tip 70 of the plunger 30 engages the IOL system component in the loading cartridge 40. With the tip 52 of the nozzle inserted into the incision in the eye, further advancement of the plunger 30 pushes the IOL system component out of the loading cartridge 40 and into the nozzle 50. As the plunger tip 70 and the IOL system component are pushed through the nozzle 50, the tapered lumen in the nozzle 50 further reduces the profile of the rolled IOL system component making it suitable for injection through a micro incision in the eye. The plunger 30 may then be advanced further until the IOL system component exits the tip 52 of the nozzle 50 and is thus delivered into the eye.

With the exception of the plunger 30 and its associated features (and the alternative loading cartridge and holder described hereinafter), the other components of the injector 10 may be similar to an injector sold under the trade name Accuject 2.2-HT from Medicel, Switzerland. As will be described in more detail hereinafter, the plunger 30 has a number of unique attributes. Thus, the features of the plunger 30 may be incorporated into other injector designs known in the art.

Figure 2:
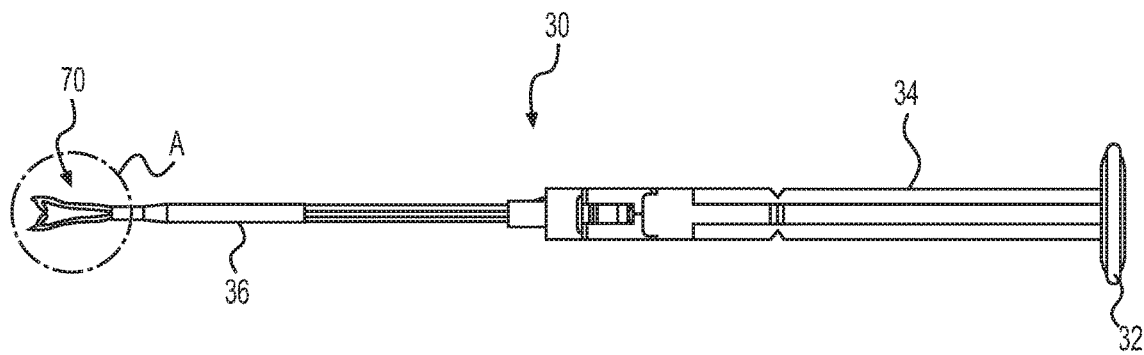
FIG. 2 is a side view of a plunger of the IOL system injector shown in FIGS. 1A and 1B.

With reference to FIG. 2, the plunger 30 is shown in more detail. As stated above, the plunger 30 includes a thumb pad 32, a proximal shaft 34, a distal shaft 36 and a tip 70. The tip 70 is shown in more detail in FIGS. 2A, 2B and 2C. Plunger tip 70 includes a first (top) arm 72 and a second (bottom) arm 74. The arms 72, 74 are connected to and extend distally from the distal shaft 36. The distal ends of the arms 72, 74 may be free as shown, with no connection therebetween.

The arms 72, 74 are flexible and pivot about their connection to the distal shaft 36 such that they that can change from an expanded configuration when disposed in the proximal end of the lumen in the nozzle 50 and a contracted configuration when disposed in the distal end of the lumen in the nozzle. The arms 72, 74 have a gap between them that decreases as the arms 72, 74 pass through the nozzle 50. In other words, the arms 72, 74 are squeezed together as the tip 70 passes through the nozzle 50. The outwards facing surfaces of the arms 72, 74 remain in contact with the inner wall of the lumen in the nozzle 50 as they pass therethrough.

Fingers 76, 78 extend inwardly in a proximal-turning curve from the arms 72, 74, respectfully. The proximal ends of the fingers 76, 78 may be attached to the arms 72, 74 at a location set back from the distal-most end of the arms 72, 74, and the distal ends of the fingers 76, 78 may be free, as shown. As best seen in FIG. 2B, the fingers 76, 78 may be laterally off-set relative to each other such that they bypass each other as the arms 72, 74 are squeezed together.

As seen in FIG. 2B, the profile of the arms 72, 74 may be configured (e.g., in an end-view rectangular profile with a height greater than a width) such that the top side of the top arm 72 and the bottom side of the bottom arm 74 remain in contact with the inner wall defining the lumen in the nozzle 50, but the lateral sides of the arms 72, 74 do not. This configuration allows the arms 72, 74 together with the fingers 76, 78 to span across the entire lumen in the nozzle 50 in one direction to prevent the tip 70 from bypassing the IOL system component as the tip 70 is advanced through the nozzle 50, which otherwise could lead to a stuck IOL in the nozzle 50. Also, because the lateral sides of the arms 72, 74 do not contact the inner wall defining the lumen in the nozzle 50, space is provided therebetween for the trailing haptic of the IOL system component if the plunger tip 70 bypasses it, allowing the haptic to be released as it exits the tip 52 of the nozzle 50, thus preventing a stuck IOL system component in the nozzle 50. This configuration also reduces friction between the tip 70 and the inner wall defining the lumen in the nozzle 50 because the only the top and bottom sides of the arms 72, 74 are in contact with the inner wall, and the lateral sides are not.

Figure 2A:
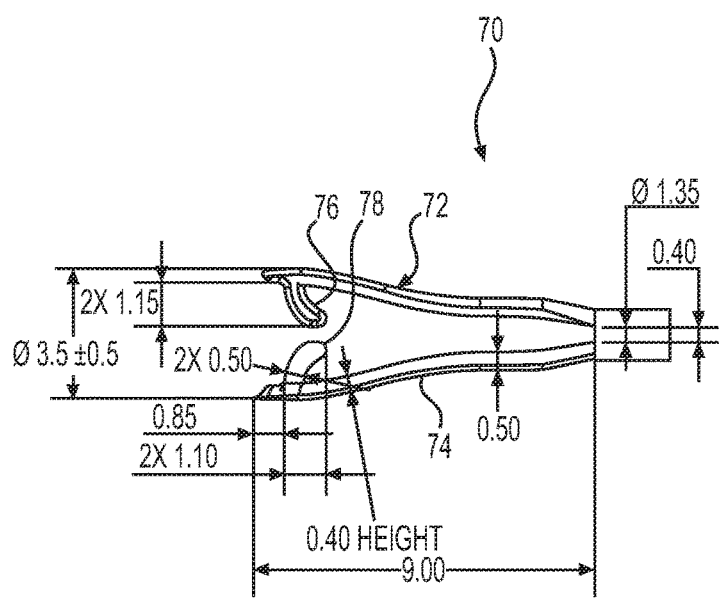
FIG. 2A is a close-up side view of a tip of the plunger shown in FIG. 2.
Figure 2B:
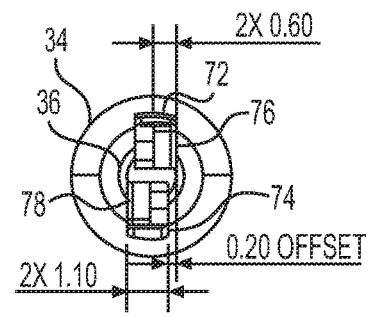
FIG. 2B is a close-up end view of the tip of the plunger shown in FIG. 2.

With continued reference to FIGS. 2A and 2B, dimensions are provided by way of example, not necessarily limitation. The arms 72, 74 may have an expanded (unconstrained) height that is greater than the inside diameter of the lumen in the nozzle 50 and greater than the outside diameter of the distal plunger shaft 36 such that they flare outwardly and distally. Each arm 72, 74 may have an overall length that is at least two times greater than their expanded height. The height and width of each arm 72, 74 may be at least five times less than their overall length and their height may taper along their length. The arms 72, 74 may be diametrically opposed (i.e., 180 degrees apart) and their overall length may be approximately equal.

Figure 2C:
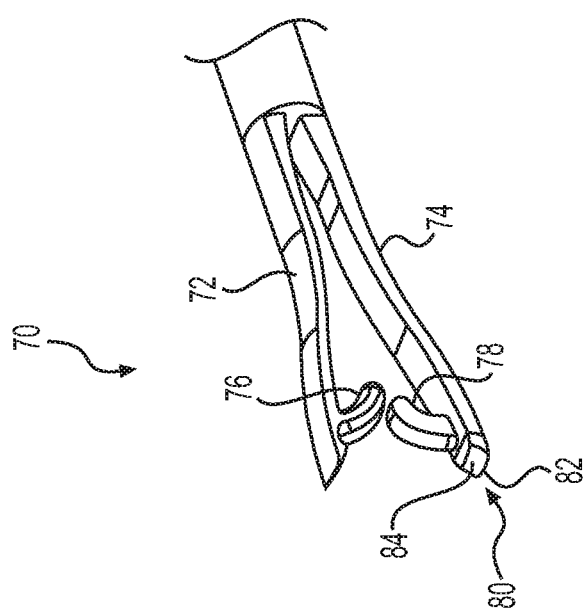
FIG. 2C is a close-up perspective view of the tip of the plunger shown in FIG. 2.

As seen best in FIG. 2C, a bevel 80 may be provided on the distal end of one or both arms 72, 74. The bevel 80 may include a distal-most edge 82 and a distal-facing surface 84. The bevel 80 may slope in a proximal and inward direction, away from the inner wall of the lumen in the nozzle 50, such that the edge 82 is in contact with the inner wall and the slope of the bevel 80 biases the IOL system component away from the inner wall. This configuration mitigates against the IOL system component becoming stuck between the tip 70 and the inner wall of the lumen in the nozzle 50 as the tip 70 is advanced through the nozzle 50.

Figure 3A:
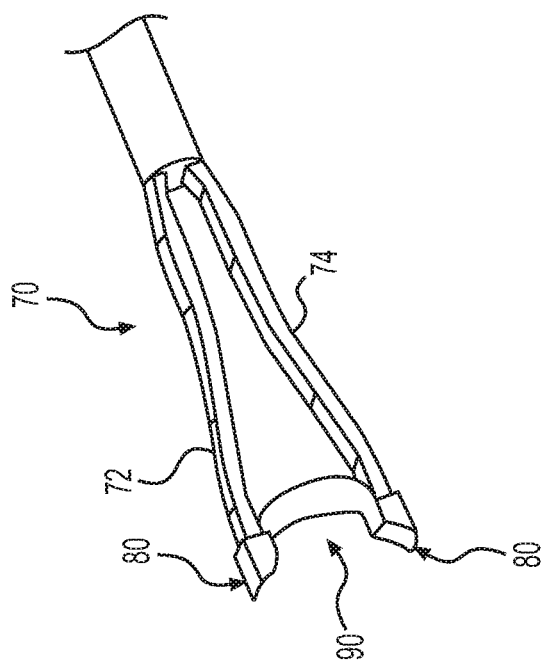
FIG. 3A is a close-up perspective view of an alternative plunger tip.

With reference to FIG. 3A, an alternative plunger tip 70 is shown in detail. In this embodiment, the plunger tip 70 does not include fingers 76, 78, but rather includes link 90 extending from and between the distal ends of the arms 72, 74. Other aspects of the plunger tip 70 may be the same or similar as described previously. Link 90 may include a hinge and/or may be formed of highly flexible material to allow it to collapse as the arms 72, 74 are squeezed together as they are advanced through the nozzle 50. This configuration allows the arms 72, 74 together with the link 90 to span across the entire lumen in the nozzle 50 in one direction to prevent the tip 70 from bypassing the IOL system component as the tip 70 is advanced through the nozzle 50, which otherwise could lead to a stuck IOL system component in the nozzle 50. The link 90 may include bevels 80 that function as described above.

Figure 3B:
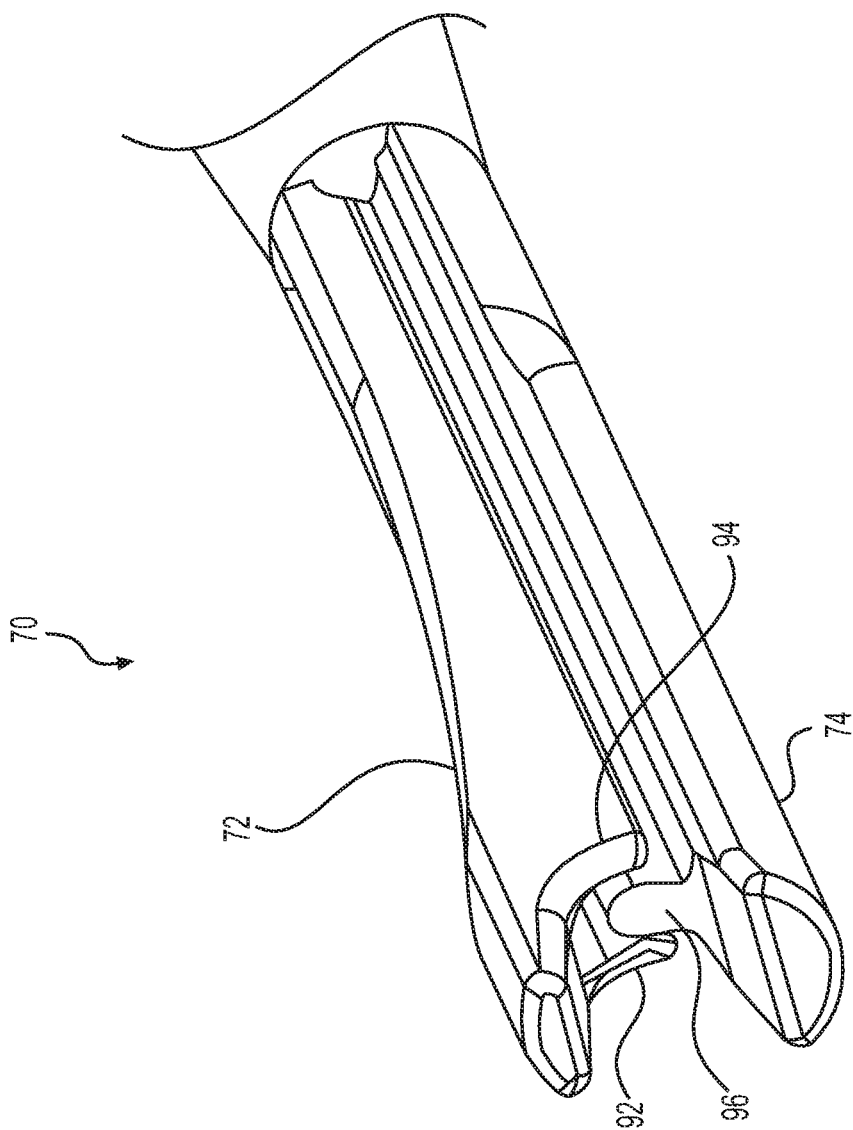
FIG. 3B is a close-up perspective view of another alternative plunger tip.

With reference to FIG. 3B, another alternative plunger tip 70 is shown in detail. In this embodiment, the plunger tip 70 does not include fingers 76, 78, but rather includes a tongue 96 extending from arm 74 into a groove defined by walls 92, 94 extending from arm 72. Other aspects of the plunger tip 70 may be the same or similar as described previously. This tongue and groove arrangement may serve the same or similar purpose as fingers 76, 78.

Figure 4A:
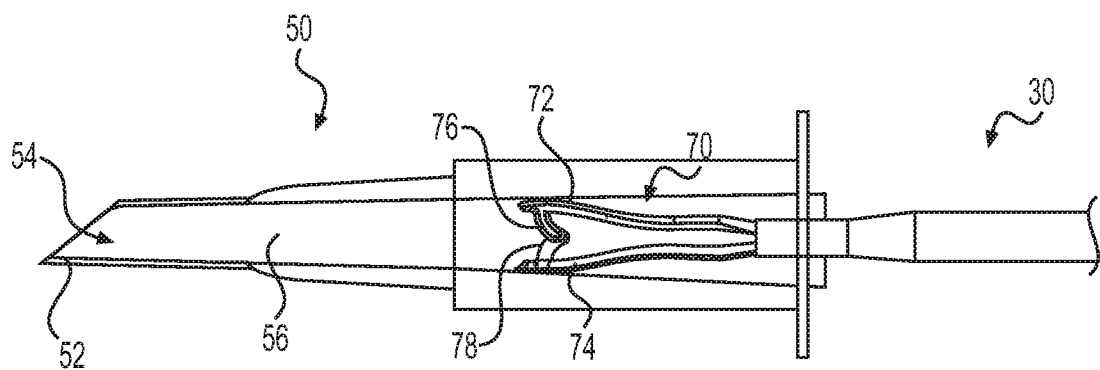
FIGS. 4A to 4C are schematic illustrations showing how the tip of the plunger of FIG. 2 is squeezed as the tip passes through a nozzle.
Figure 4B:
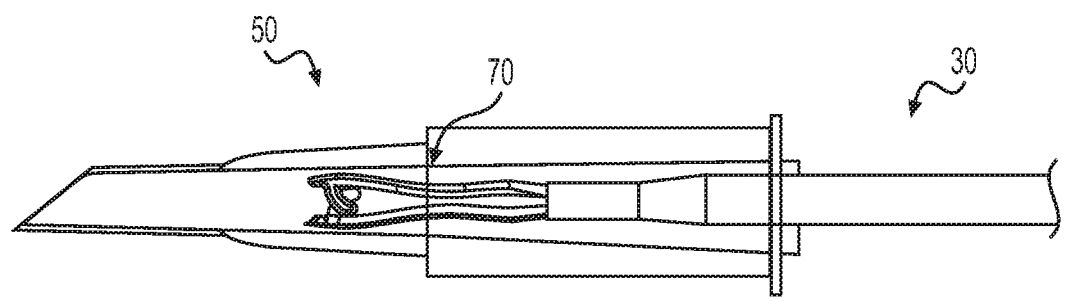
Figure 4C:
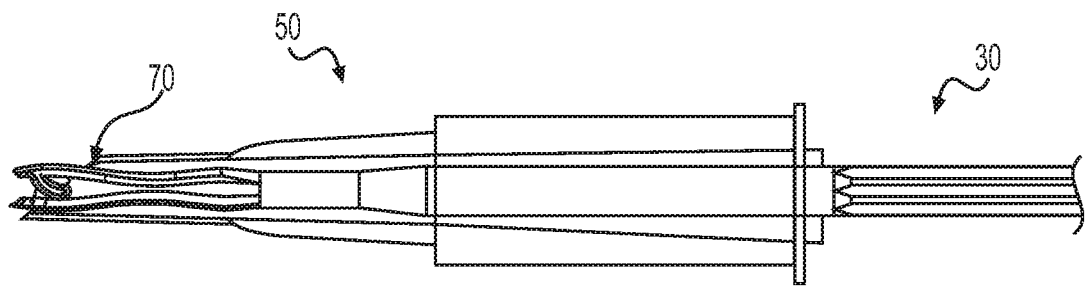

With reference to FIGS. 4A-4C, advancement of the plunger tip 70 through the lumen in the nozzle (a.k.a. cartridge tip) 50 is schematically illustrated in step-wise fashion. For this purpose, the nozzle 50 is shown in transparent view with distal beveled tip 52, distal opening 54 and through lumen 56, and only a distal portion of the plunger 30 including tip 70 is shown. As mentioned previously, the cross-sectional area or diameter of the lumen 56 in the nozzle 50 gradually decreases from proximal to distal end. As such, the arms 72, 74 are gradually squeezed together as the tip and IOL (not shown) pass through the nozzle 50. In FIG. 4A, the arms 72, 74 are in an expanded state when in a proximal portion of the nozzle 50. In FIG. 4B, as the tip 70 is advanced, the arms 72, 74 are squeezed by the inner walls defining the nozzle lumen 56 and are changing to a compressed or contracted state. In FIG. 4C, the arms 72, 74 are in a contracted state when in a distal portion of the nozzle 50. Note in FIG. 4A that the distal ends of the fingers 76, 78 are bypassing each other, in FIG. 4B they are abutting the inside surface of the arms 72, 74, and in FIG. 4C they are bent inward. All the while, the arms 72, 74 together with the fingers 76, 78 span across the entire lumen 56 in at least one direction (but not all) to keep the IOL system component in front of the tip 70 and prevent the IOL system component from becoming stuck between the tip 70 and the inner wall of the nozzle lumen 56. In a plane orthogonal to the one illustrated, it would be apparent that the lateral sides of the arms 72, 74 and the fingers 76, 78 are not in contact with the inner wall of the nozzle lumen 56, thereby reducing friction.

The injector 10 may be used with a wide variety of IOL system components including modular IOL system components and non-modular IOLs (e.g., unitary and/or monolithic IOLs). By way of example, not limitation, the injector may be used to inject a base component and an optic component that form a modular IOL system when assembled. The base and optic may be injected into the eye separately and assembled in the eye, or assembled outside the eye and injected into the eye together. A description of an example base component 400 is provided with reference to FIGS. 5 and 5A, and a description of an example optic component 500 is provided with reference to FIG. 6. Further details regarding a similar modular IOL system configuration may be found in U.S. Non-provisional patent application Ser. No. 15/585,901, filed May 3, 2017 and entitled Intraocular Lens Designs for Improved Stability, which is incorporated herein by reference.

Figure 5:
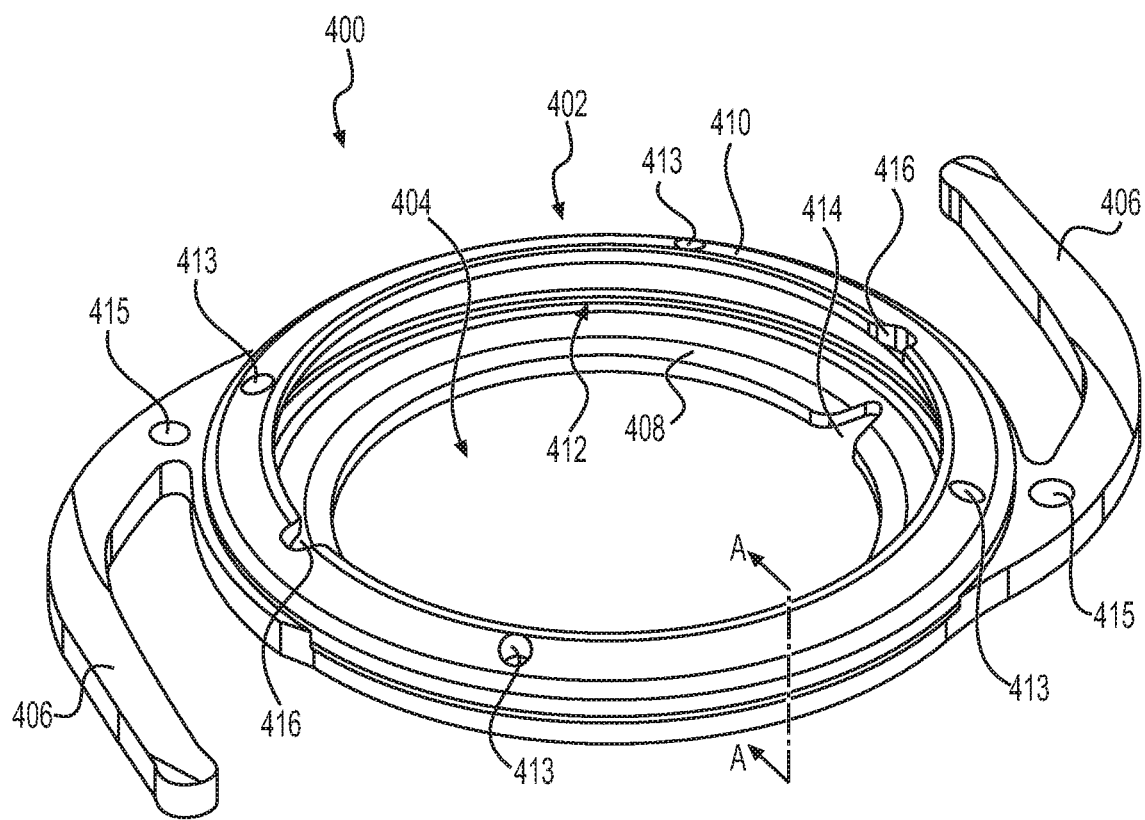
FIG. 5 is a perspective view of a base of a modular IOL system.

With reference to FIG. 5, the base 400 includes an annular ring 402 defining a center hole 404. A pair of haptics 406 extend radially outward from the annular ring 402. The annular ring 402 includes a lower rim 408, an upper rim 410 and an inward-facing recess 412, into which the lens 500 may be inserted to form the modular IOL system.

The lower rim 408 may include a pair of diametrically opposed (180 degrees) folding notches 414, and the upper rim 410 may include a corresponding pair of folding notches 416. Folding notches 414, 416 may be aligned with the mid portions of the haptics 406 and are configured to provide a natural folding crease to fold the base in half in the loading cartridge 40 of the injector 10, thereby aligning the mid portion of the haptic with the plunger tip 70. Notches 414, 416 may also provide access for a probe (e.g., Sinskey hook) intra-operatively, which allows the base 400 to be more easily manipulated. The haptics 406 may include holes 415 adjacent the annular ring 402 for intraoperative manipulation with a probe. A series of vent holes 413 may be distributed around the upper rim 410.

Figure 5A:
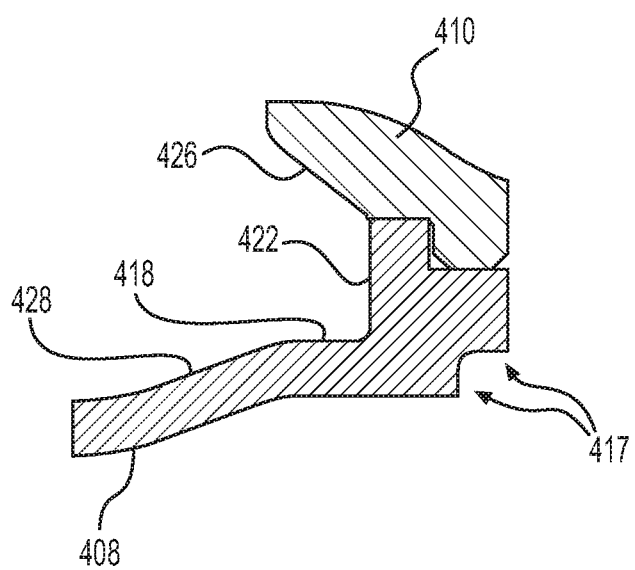
FIG. 5A is a cross-sectional view taken along line A-A in FIG. 5.

With reference to FIG. 5A, which is a cross sectional view taken along line A-A in FIG. 5, the recess 412 may have a tapered profile defined by horizontal posterior surface 418, a vertical lateral or outer surface 422 and a flared anterior surface 426 extending radially inward and anteriorly outward from the vertical outer surface 422. The inside diameter of the posterior rim 408 may be smaller than the inside diameter of the anterior rim 410. With this arrangement, the lens 500 may be placed through the circular opening 404 defined by the anterior rim 410 to land or rest upon the posterior rim 408, and the flared anterior wall 426 together with the flared posterior wall 428 may act as a funnel to guide the tabs 504 and 506 of the lens 500 into the deep portion of the recess 412. A pair of square edges 417 may extend around the posterior periphery of the annular ring 402 to help reduce cellular proliferation (posterior capsular opacification or PCO) onto the lens 500.

Figure 6:
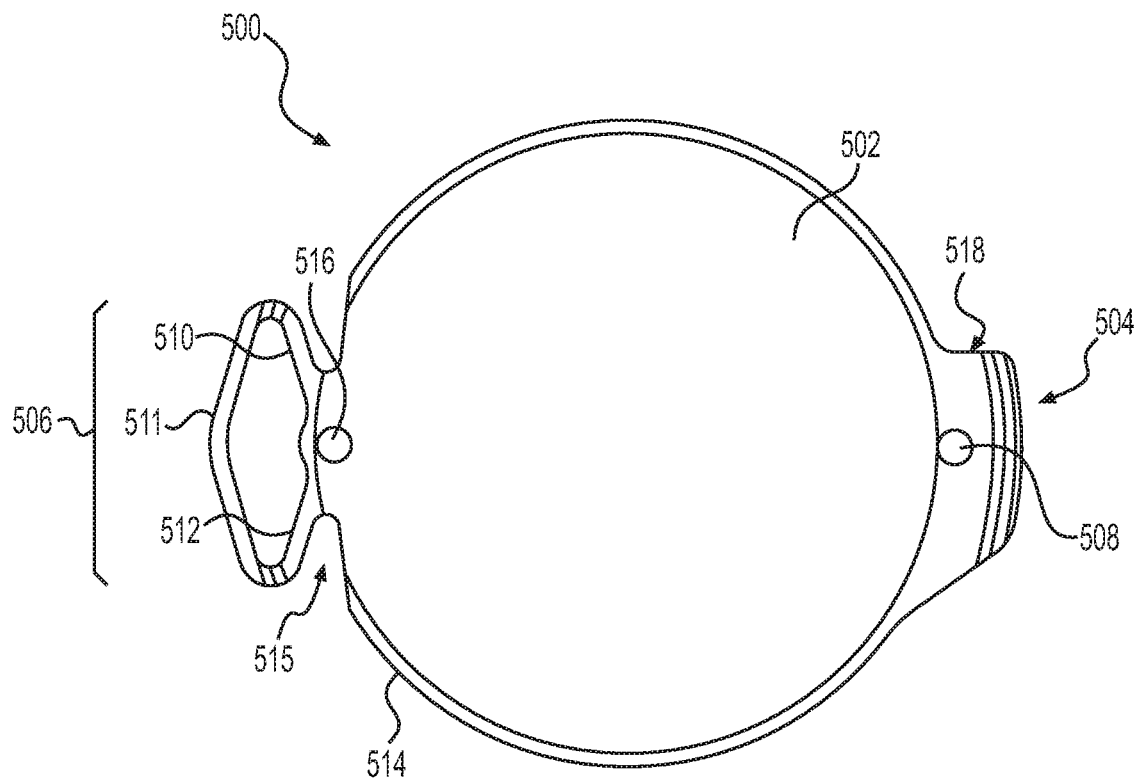
FIG. 6 is a top view of a lens of a modular IOL system.

With reference to FIG. 6, a top (anterior) view of the lens 500 is shown. The lens 500 may include an optic portion 502 and one or more tabs 504 and 506. As shown, tab 504 is fixed, whereas tab 506 may be actuated. In one example, tab 504 is more resistant to deformation (e.g., compression and/or expansion) in a radial direction than tab 506. Fixed tab 504 may include a thru hole 508 so that a probe (e.g., Sinskey hook) or similar device may be used to engage the hole 508 and manipulate the tab 504. Actuatable tab 506 may be actuated between a compressed position for delivery into the hole 404 of the base 400, and an uncompressed extended position (shown) for deployment into the recess 412 of the base 400, thus forming an interlocking connection between the base 400 and the lens 500. It also is contemplated that actuatable tab 506 may be inserted into recess 412, and may be actuated between the compressed position to facilitate entry of fixed tab 504 into recess 412, and the uncompressed extended position to insert fixed tab 504 further into recess 412 to form the interlocking connection between base 400 and lens 500.

Actuatable tab 506 may include two arms 510 and 512 that extend radially outward in different (e.g., opposite) directions. In one example, an obtuse angle may be formed between the directions. Each arm 510, 512 may have one end connected to the edge of the optic 502 and the other end connected to middle arm 511. Hinge portions may connect ends of arms 510 and 512 to optic 502, and may connect other ends of arms 510 and 512 to middle arm 511. Each of arms 510, 511, and 512 may include one or more linear portions. In one example, middle arm 511 may include two linear portions meeting at a mid-portion of middle arm 511. Middle arm 511 may be angled radially inward as shown with an apex in the mid-portion thereof. The apex may be a hinge portion. Portions of optic 502 and arms 510, 511, and 512 may form a ring around a aperture through actuatable tab 506. Dimensions of that aperture may change as actuatable tab 506 moves between compressed and extended states.

With this configuration, the actuatable tab 506 may bend along all three arms 510, 511, 512, and/or may bend along the hinge portions, when moving between its compressed and extended states, but may provide a single portion (apex of middle arm 511) for initial insertion into recess 412 of base 400. A rim 514 may extend around the perimeter of the optic 502, terminating shy of the arms 510 and 512, thus allowing the arms 510 and 512 to fully compress against the edge of the optic 502. The edge of optic 502 may be planar, and may contact one or more planar surfaces of arm 510 and/or arm 512. The rim 514 of the lens 500 may have an outside diameter that is greater than the inside diameter of the posterior rim 408 of the base 400 such that the lens 500 doesn't fall through the opening 404 of the base 400 and such that the lens 500 is circumferentially supported around its perimeter by the posterior rim 408 of the base 400. A gusset with a guide hole 516 may be disposed between the two arms 510 and 512 to facilitate manipulation by a probe. Similarly, a guide hole 508 may be provided in the fixed tab 504 to provide access for a probe (e.g., Sinskey hook) or similar device to manipulate the fixed tab 504 into the recess 412 in the base 400. A notch 518 may be provided in the fixed tab 504 to provide asymmetry as a visual indicator that the anterior side is up (rather than down) when the notch is counter-clockwise of the hole 508.

The base 400 and lens 500, including the alternative embodiments described herein, may be formed by cryogenically machining and polishing hydrophobic acrylic material. Optionally, the base 400 may be manufactured by forming two (anterior and posterior) components and adhesively connecting them together. For example, the two components may be cryogenically machined hydrophilic acrylic connected together by a U.V. curable adhesive. Alternatively, the two components may be formed of different materials adhesively connected together. For example, the anterior component may be formed of hydrophilic acrylic which does not adhere to ocular tissue, and the posterior component may be formed of hydrophobic acrylic which does adhere to ocular tissue.

As a further alternative, the base 400 may be manufactured by cryogenic machining the first component and over-molding the second component. The first component may include geometric features that become interlocked when over-molded, thus mitigating the need for adhesive to connect the components. For example, the base 400 may be manufactured by cryogenic machining of hydrophilic acrylic to form the posterior component, and over-molding the anterior component of a moldable material such as silicone.

Whether made of a single component, two components adhesively connected, or two components with one component molded over the other, all or a portion of the annular ring 402 may include coloration to enhance the ability to visualize the tabs 504, 506 relative to the recess 412 to better determine if the tabs 504, 506 are anterior to, inside or posterior to the recess 412. In this embodiment, the annular ring 402 may be a first color and the tabs 504, 506 may be a second (different) color. Alternatively, if the annular ring 402 comprises an anterior component and a posterior component, either or both of the anterior and posterior components may be a first color and the tabs 504, 506 may be a second (different) color. By way of example, the annular ring 402 may be a blue color (blue dye monomer additive) and the tabs 504, 506 may be a natural (transparent) color. In this example, when viewed anterior to posterior, and because the anterior rim 410 has a larger inside diameter than the posterior rim 408, the inside portion of the posterior rim 408 may appear light blue, and the overlap of the anterior rim 410 and posterior rim 408 may appear dark blue. With this differentiation in color, the position of the tabs 504, 506 relative to the recess 412 may be visually more apparent to more easily facilitate assembling the optic 500 to the base 400.

As may be appreciated from the forgoing description, the optic 500 may be similarly sized to a conventional IOL and the base 400 may be slightly larger to allow the optic 500 to fit therein. A conventional loading cartridge may be used for both the base 400 and the optic 500. However, it may be desirable to use a modified loading cartridge 40 for the base as described with reference to FIG. 7-7C.

Figure 7:
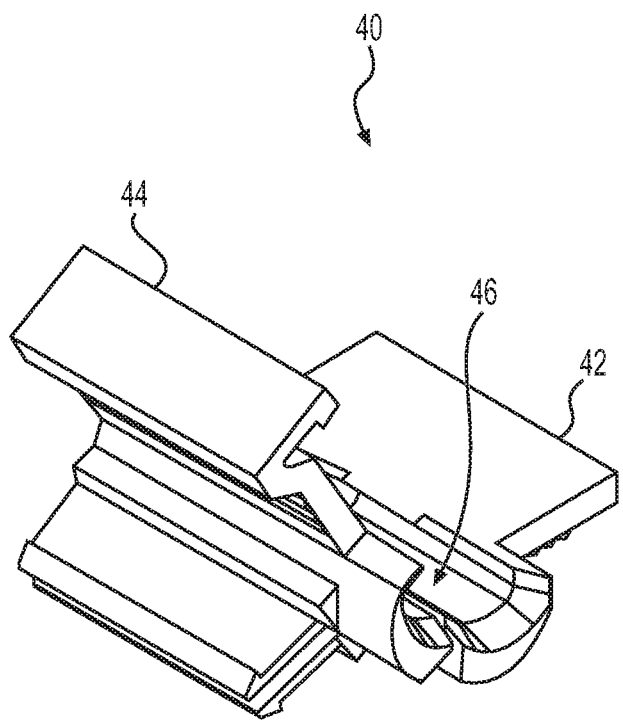
FIG. 7 is a perspective view of a loading cartridge for use in the IOL system injector shown in FIGS. 1A and 1B.
Figure 7A:
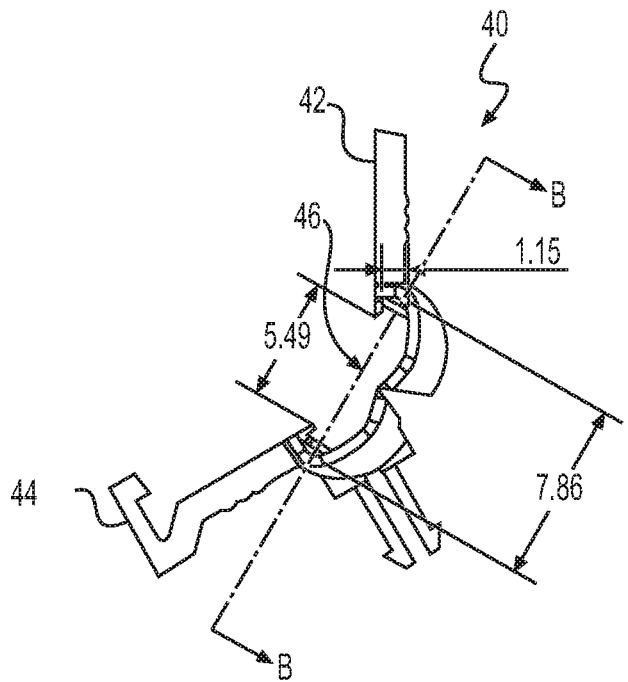
FIG. 7A is an end view of the loading cartridge shown in FIG. 7.
Figure 7B:
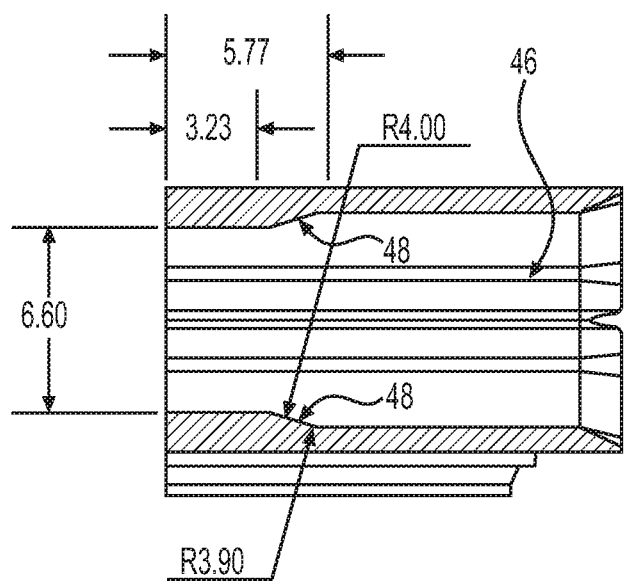
FIG. 7B is a cross-sectional view taken along line B-B in FIG. 7A.

With specific reference to FIGS. 7 and 7A, the loading cartridge 40 includes a first folding wing 42, a second folding wing 44 with a locking mechanism, and a chamber 46 configured to hold the base 400 when the wings 42, 44 are closed. With reference to FIG. 7B, which is a cross-sectional view taken along line B-B in FIG. 7A, the sides of the chamber may include shoulders 48 such that a proximal width of the chamber 46 is wider than a distal width of the chamber 46. By way of example, not limitation, the proximal width may be about 7.9 mm and the distal width may be about 6.6 mm. This configuration defines a tapered chamber lumen that gradually compresses the relatively larger base 400 into the proximal portion of the nozzle lumen 56 as the plunger 30 pushes the base 400 distally. In addition, as seen in FIG. 7C, the shoulders 48 abut the annular ring 402 of the base 400 thereby providing a backstop for the base 400 to maintain the axial (longitudinal) position of the base 400 in the loading cartridge 40, particularly when the tip 70 of the plunger 30 engages the proximal side of the base 400. The folding notches 414 of the base 400 may be aligned with the longitudinal axis of the loading cartridge 40 to provide a hinge for uniform diametric folding of the base 400 when the wings 42, 44 of the cartridge 40 are closed.

Figure 8:
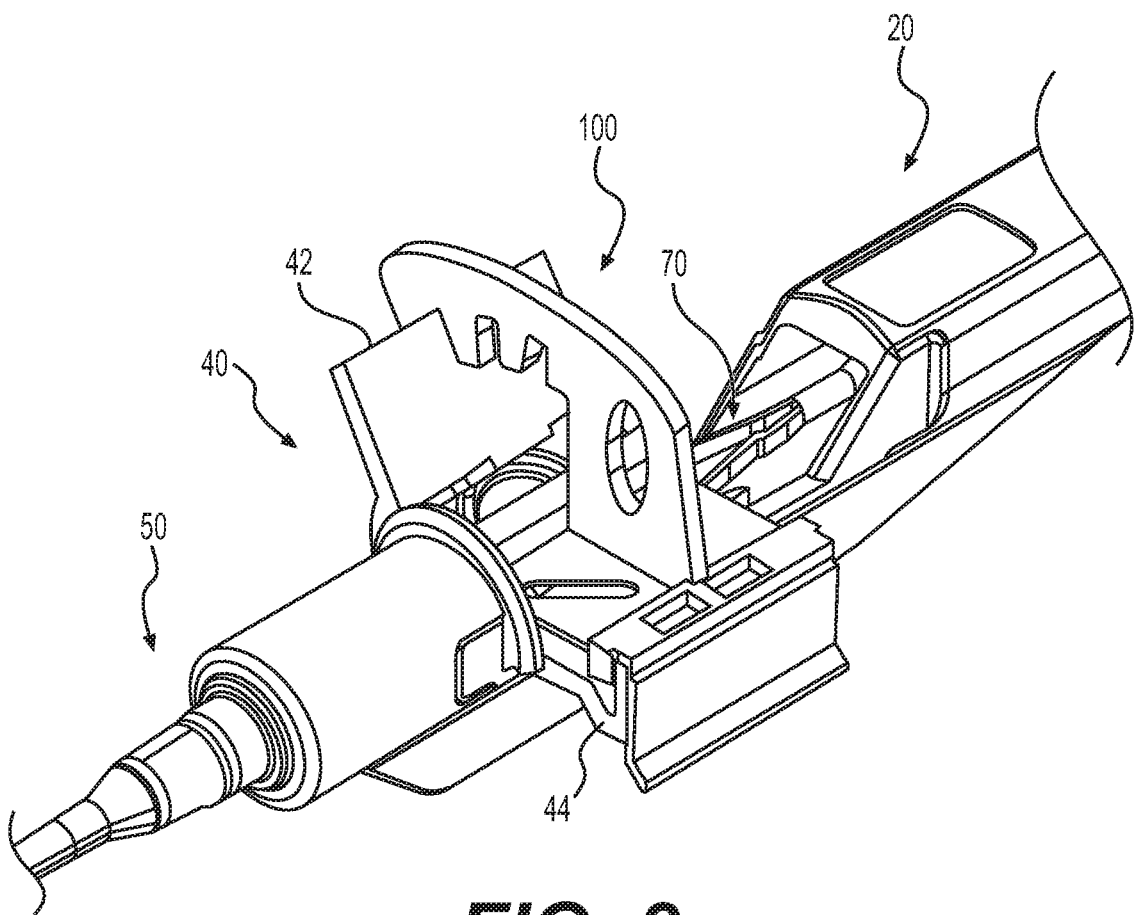
FIG. 8 is a perspective view of an alternative holder for use in the IOL system injector shown in FIG. 1.
Figure 8A:
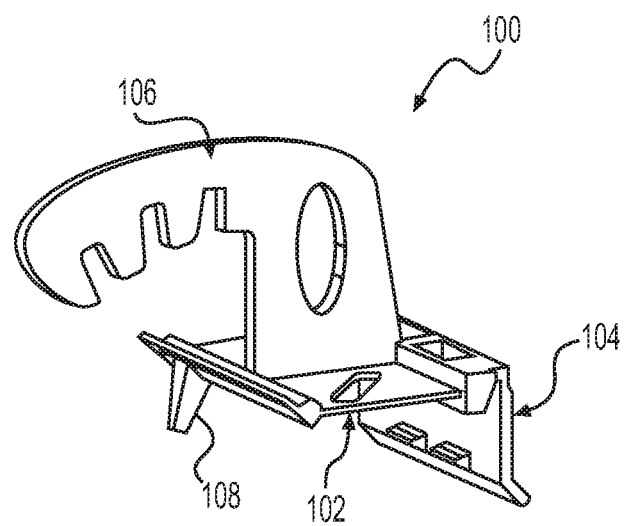
FIG. 8A is a close-up perspective view of the holder shown in FIG. 8.
Figure 8B:
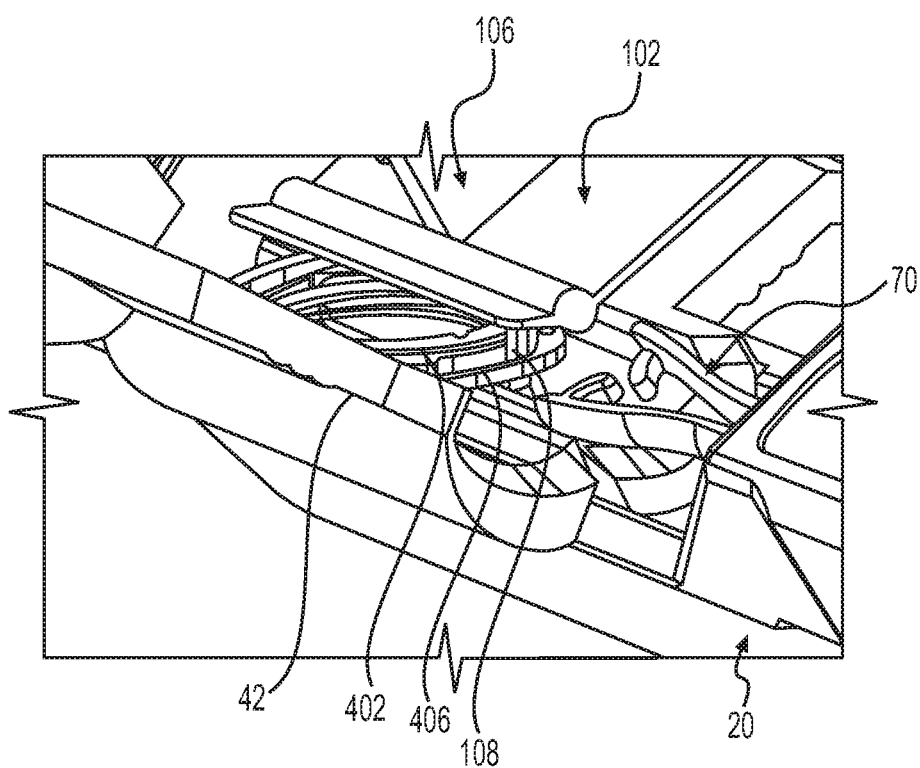
FIG. 8B is a close-up perspective view of the holder shown in FIG. 8 with a base positioned therein.

As described previously, the base 400 and/or optic 500 may be loaded or pre-loaded in the chamber 46 of the loading cartridge 40. If pre-loaded, a holder 100 may be used to hold the base 400 or optic 500 in the chamber 46 of the loading cartridge 40 while packaged and shipped as shown in FIGS. 8-8B. Holder 100 may include a holding plate 102, a connector portion 104, an arm 106 and a retaining pin 108. The holding plate 102 may cover all or a portion of the base 400 or optic 500 in the chamber 46. The connector portion 104 may attach to the wing 44 of the cartridge 44, and the arm 106 may engage the other wing 42 of the cartridge 40 via one or more slots. The retaining pin 108 may extend from a lateral edge of the holding plate 102 at position recessed from a proximal edge of the holding plate 102 such that it is positioned between the annular ring 402 and the trailing or proximal haptic 402 of the base 400 as shown in FIG. 8B. This arrangement, when combined with the shoulders 48 of the cartridge, retain the base 400 and limit movement in all directions during packaging and shipping.

The foregoing discussion of the disclosure has been presented for purposes of illustration and description. The foregoing is not intended to limit the disclosure to the form or forms disclosed herein. Although the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. An intraocular lens system, comprising:
   a base, comprising:
   an annular body including an upper rim and a lower rim,
   an opening extending through the annular body in an axial direction of the annular body,
   a first pair of diametrically opposed folding notches in the upper rim, and a second pair of diametrically opposed folding notches in the lower rim, the first pair and the second pair of diametrically opposed folding notches configured to provide a folding crease for folding the base, and
   a recess extending circumferentially about the opening; and
   a lens, wherein the lens is insertable into and removable from the recess, the lens comprising:
   a central optic,
   a first tab protruding radially away from the central optic, and
   a second tab protruding radially away from the central optic,
   wherein the second tab is more resistant to compression in a radial direction than the first tab, and
   wherein the first tab includes:
   a first arm protruding radially away from the central optic,
   a second arm protruding radially away from the central optic and extending away from the first arm, and
   a third arm extending from the first arm to the second arm, wherein movement of one or more of the first, second, and third arms results in deformation of the first tab.

2. The intraocular lens system of claim 1, wherein a central portion of the third arm includes an apex of the third arm, the apex being a radially-outermost portion of the third arm.

3. The intraocular lens system of claim 2, wherein the third arm has a first linear section and a second linear section, the first and second linear sections being linked at the apex.

4. The intraocular lens system of claim 1, wherein each of the first, second, and third arms has at least one linear section.

5. The intraocular lens system of claim 4, wherein an obtuse angle is formed between the first and second linear sections.

6. The intraocular lens system of claim 1, wherein the first arm extends from the central optic in a first direction, the second arm extends from the central optic in a second direction, the second direction being a different direction from the first direction, and wherein an obtuse angle is formed between the first and second directions.

7. The intraocular lens system of claim 1, wherein the second tab includes:
a first side projecting from a first radially-outer surface of the central optic, wherein a first angle is formed between the first side and the first radially-outer surface, and
a second side projecting from a second radially-outer surface of the central optic, wherein a second angle is formed between the second side and the second radially-outer surface,
wherein magnitudes of the first and second angles are different.

8. An intraocular lens system, comprising:
a base, comprising:
an annular body including an upper rim and a lower rim,
an opening extending through the annular body in an axial direction of the annular body,
a first pair of diametrically opposed folding notches in the upper rim, and a second pair of diametrically opposed folding notches in the lower rim, the first pair and the second pairs of diametrically opposed folding notches configured to provide a folding crease for folding the base, and
a recess extending circumferentially about the opening; and
a lens, wherein the lens is configured for insertion into and removable from the recess, the lens comprising:
a central optic,
a first tab extending radially away from the central optic, and
a second tab extending radially away from the central optic, wherein the second tab is more resistant to compression than the first tab,
wherein the first tab includes:
a first arm extending radially away from the central optic,
a second arm extending radially away from the central optic,
a third arm extending between the first arm with the second arm,
wherein one or more of the first, second, and third arms is configured to deform to move the first tab between a compressed state and an extended state, and wherein in the extended state of the first tab, an obtuse angle is formed between the first and second arms.

9. The intraocular lens system of claim 8, wherein:
the first tab includes a first planar surface, and
the central optic includes a second planar surface.

10. The intraocular lens system of claim 8, wherein the central optic includes a planar surface.

11. The intraocular lens system of claim 8, wherein:
the first arm includes a first hinge portion,
the second arm includes a second hinge portion, and
the third arm includes a third hinge portion, wherein the first, second, and third hinge portions are configured to bend as the first tab moves between the extended and compressed states.

12. The intraocular lens system of claim 8, wherein the first, second, and third arms, and the central optic, form a closed ring surrounding an aperture, and wherein a width of the aperture narrows as the first tab moves to the compressed state.

13. A method for assembling an intraocular lens system, the method comprising:
inserting one of: (a) a first tab and (b) a second tab, of a lens of the intraocular lens system, into a recess of a base of the intraocular lens system, the second tab being more resistant to compression than the first tab,
wherein the lens includes a central optic, the first tab extending radially away from the central optic, and the second tab extending radially from the central optic,
wherein the first tab includes:
a first arm extending radially away from the central optic,
a second arm extending radially away from the central optic and away from the first arm, and
a third arm linking the first and second arms,
wherein the base includes:
an annular body including an upper rim and a lower rim,
a first pair of diametrically opposed folding notches in the upper rim, and a second pair of diametrically opposed folding notches in the lower rim, the first pair and the second pair of diametrically opposed folding notches configured to provide a folding crease for folding the base, and
an opening extending through the annular body in an axial direction of the annular body, the recess extending circumferentially about the opening; and
inserting the other of the first and second tabs into the recess, wherein the other of the first and second tabs is inserted into the recess while the at least one of the first and second tabs is in the recess.

14. The method of claim 13, wherein:
inserting one of the first and second tabs into the recess includes inserting the second tab into the recess,
inserting the other of the first and second tabs into the recess includes inserting the first tab into the recess, and
inserting the first tab into the recess includes moving the first tab from an extended state to a compressed state by moving the first, second, and third arms towards the central optic, to position the first tab such that the first tab enters the recess as the first tab moves from the compressed state to the extended state.

15. The method of claim 13, wherein:
inserting one of the first and second tabs into the recess includes inserting the first tab into the recess, and
inserting the second tab into the recess includes moving the first tab from an extended state to a compressed state by moving the first, second, and third arms towards the central optic, to position the second tab such that the second tab enters the recess as the first tab moves from the compressed state to the extended state.

16. The method of claim 13, wherein inserting the first tab into the recess includes inserting an apex of the third arm into the recess, the apex of the third arm being at a central portion of the third arm, and the apex being a radially-outermost portion of the third arm.

17. The method of claim 13, further including manipulating the lens using one or more tools, and wherein the one or more tools are inserted into at least one of a plurality of holes in the lens, wherein the plurality of holes includes a first hole where the first tab meets the central optic and a second hole wherein the second tab meets the central optic.

18. The method of claim 13, further including guiding at least one of the first and second tabs into the recess by engaging the at least one of the first and second tabs with an anterior wall of the recess, the anterior wall forming an obtuse angle with a radially-outer wall of the recess wherein the anterior and radially-outer walls meet.

\* \* \* \* \*